(12) United States Patent
Du et al.

(10) Patent No.: US 11,324,217 B2
(45) Date of Patent: May 10, 2022

(54) PREPARATION METHOD AND APPLICATION OF POLYKETIDES BEARING THE TRANS-FUSED DECALIN SKELETON

(71) Applicant: QINGDAO AGRICULTURAL UNIVERSITY, Qingdao (CN)

(72) Inventors: Fengyu Du, Qingdao (CN); Lin Xiao, Qingdao (CN)

(73) Assignee: QINGDAO AGRICULTURAL UNIVERSITY, Shandong (CN)

( * ) Notice: Subject to any disclaimer, the term of this patent is extended or adjusted under 35 U.S.C. 154(b) by 171 days.

(21) Appl. No.: 16/989,851

(22) Filed: Aug. 10, 2020

(65) Prior Publication Data

US 2021/0092953 A1 Apr. 1, 2021

Related U.S. Application Data

(63) Continuation of application No. PCT/CN2020/072772, filed on Jan. 17, 2020.

(30) Foreign Application Priority Data

Sep. 26, 2019 (CN) .......... 201910914239.2
Jan. 10, 2020 (CN) .......... 202010024297.0

(51) Int. Cl.
*A01N 37/38* (2006.01)
*A01N 25/14* (2006.01)
*A01N 35/04* (2006.01)
*C12P 7/26* (2006.01)
(Continued)

(52) U.S. Cl.
CPC ............. *A01N 37/38* (2013.01); *A01N 25/14* (2013.01); *A01N 35/04* (2013.01); *C12P 7/26* (2013.01); *C12P 7/62* (2013.01)

(58) Field of Classification Search
CPC ........ A01N 37/38; A01N 25/14; A01N 35/04; A01N 63/36; C12P 7/26; C12P 7/62
See application file for complete search history.

(56) References Cited

FOREIGN PATENT DOCUMENTS

| CN | 109422651 A | 3/2019 |
|---|---|---|
| CN | 110563569 A | 12/2019 |
| DE | 102004005106 A1 | 8/2005 |

OTHER PUBLICATIONS

Wang et al., Herbicidal Polyketides and Diketopiperazine Derivatives from Penicillium viridicatum, 2019, J. Agric. Food Chem., 67, 14102-14109. (Year: 2019).*

(Continued)

*Primary Examiner* — Trevor Love
(74) *Attorney, Agent, or Firm* — SZDC Law P.C.

(57) ABSTRACT

A method of isolating a compound 1 and a compound 2 includes: providing *Penicillium* sp. TR85; inoculating the *Penicillium* sp. TR85 into a sterilized solid medium; resting for fermentation at room temperature, and obtaining a fermentation product. The fermentation product includes the compound 1 and the compound 2. An herbicidal composition includes a compound 1 or a compound 2; and pesticide-acceptable adjuvants.

1

(Continued)

-continued

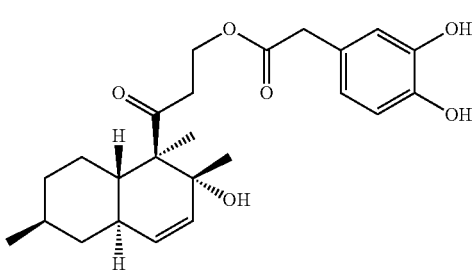

2

7 Claims, 5 Drawing Sheets

Specification includes a Sequence Listing.

(51) Int. Cl.
 *C12P 7/62* (2022.01)
 *A01N 63/36* (2020.01)

(56) References Cited

OTHER PUBLICATIONS

Maria P. Sobolevskaya et al., "Pallidopenillines: Polyketides from the Alga-Derived Fungus Penicillium thomii Maire KMM 4675," Journal of Natural Products Nov. 29, 2016.

* cited by examiner

PREPARATION METHOD AND APPLICATION OF POLYKETIDES BEARING THE TRANS-FUSED DECALIN SKELETON

The present application is a Continuation Application of PCT/CN2020/072772, filed on Jan. 17, 2020, which claims priority to Chinese Application Nos. 201910914239.2, filed on Sep. 26, 2019, and 202010024297.0, filed on Jan. 10, 2020, which are incorporated by reference for all purposes as if fully set forth herein.

BACKGROUND OF THE INVENTION

1. Technical Field

The invention relates to the technical field of microbial pesticides, specifically polyketone compounds with a trans-naphthane ring obtained from a solid fermentation product of the strain *Penicillium* sp. TR85, and a separation and purification method thereof and an application thereof in weeding.

2. Description of Related Art

Weeds and crops compete for nutrition and growth space, which not only causes a reduction in crop yield, but also disrupts the ecological balance in the field, so weed control is of great significance to agricultural production. *Echinochloa crusgalli* is a worldwide malignant weed. Among the main weeds in paddy fields in China, *Echinochloa crusgalli* has the largest occurrence and damage area, accounting for about 43% of the total paddy field area. For a long time, although chemically synthesized herbicides can effectively control weeds, they have caused problems such as environmental pollution and weed's resistance to the herbicides. Moreover, long-term excessive use of pesticides has also caused pesticide residues to exceed the standard, endangering the safety of agricultural products and human health. Finding herbicidal active ingredients from microorganisms, plants and other biological resources has the advantages of low toxicity, good environmental compatibility and low herbicide resistance. It has become an important source for the development of "environmentally friendly" herbicides.

According to literature research, polyketone compounds with a trans-naphthane ring have antibacterial, antitumor and immunomodulatory activities, and no related reports have been reported on their herbicidal activity. The two polyketone compounds with a trans-naphthane ring involved in the invention are new compounds, and for the first time, the polyketone compounds with a trans-naphthane ring have been found to have herbicidal potential, and their structures are significantly different from known commercial herbicides. This provides guidance for the further development of novel biogenic herbicides.

BRIEF SUMMARY OF THE INVENTION

The invention is intended to provide polyketone compounds with a trans-naphthane ring and a preparation method and application thereof.

To achieve the above objectives, the technical solutions of the invention are as follows:

A method of isolating a compound 1 and a compound 2 includes: providing *Penicillium* sp. TR85; inoculating the *Penicillium* sp. TR85 into a sterilized solid medium; resting for fermentation at room temperature, and obtaining a fermentation product. The fermentation product includes the compound 1 and the compound 2.

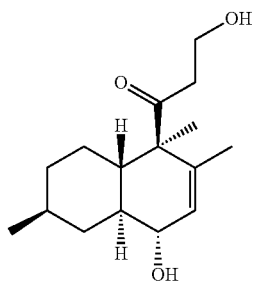

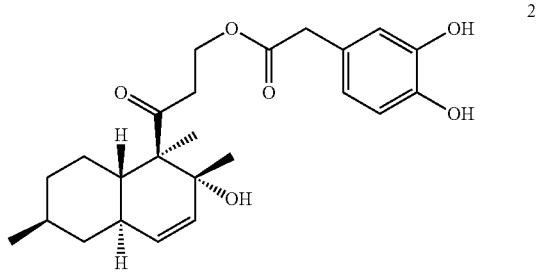

The sterilized solid medium includes rice, peptone and see water in a ratio of 100 g:0.6 g:100 mL.

The further includes: (1) soaking and extracting the fermentation product with ethyl acetate to obtain extracts, and combining and concentrating the extracts to obtain a crude fermentation extract; (2) carrying out a reduced-pressure silica gel column chromatography on the crude fermentation extract, performing a gradient elution with an eluent: petroleum ether:ethyl acetate at a gradient of 40:1 to 1:1 (v/v), collecting an eluting fraction when the petroleum ether:ethyl acetate is at a gradient of 1:1, carrying out a reversed-phase silica gel column chromatography, and performing a gradient elution with a second eluent: methanol:water solution at a gradient of 2:8 to 1:0 (v/v); (3) collecting reversed-phase silica gel eluting fractions when methanol:water is at a gradient of 6:4 (v/v), carrying out a semi-preparative high performance liquid chromatography with 50% methanol in water as a mobile phase, a detection wavelength of 220 nm, and a flow rate of 3 mL/min, and collecting fractions with a retention time $t_R$ of 14.4 min, thus obtaining the compound 1; and (4) collecting reversed-phase silica gel eluting fractions when the methanol:water is at a gradient of 8:2 (v/v), carrying out a semi-preparative high performance liquid chromatography with 76% methanol in water as a mobile phase, a detection wavelength of 220 nm, and a flow rate of 3 mL/min, and collecting fractions with retention time $t_R$ of 12.5 min, thus obtaining the compound 2.

An herbicidal composition includes a compound 1 or a compound 2; and pesticide-acceptable adjuvants.

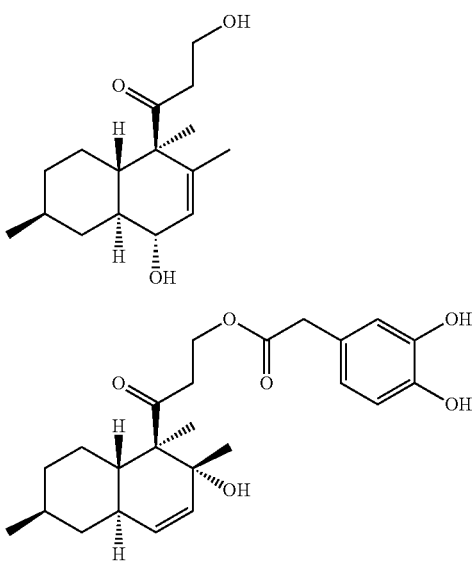

The pesticide-acceptable adjuvants are selected from the group consisting of carriers, surfactants and safeners.

The herbicidal composition further includes one or more selected from the group consisting of a stabilizer, a chelating agent, a dye, a colorant, a protective colloid, a binder, a thickener, a thixotropic agent, a penetrant and a polymer.

The herbicidal composition is an oil, an emulsion, a suspension, or a wettable powder.

The compounds of the invention may be combined with other herbicides in the form of a composition; the composition includes the compound represented by formula (I) and a pesticide-acceptable salt and/or solvate as an active ingredient, and a pesticide-acceptable carrier. The compound of the invention can be used in combination with other active ingredients, as long as there is no antagonistic effect between them.

The herbicide of the invention may also contain pesticide-acceptable conventional adjuvants, which may be carriers, surfactants and safeners; according to the adjuvant composition of the herbicide, the herbicide can be prepared into any desired preparation form, such as missible oil, a suspending agent, a microemulsion, dispersible oil suspension, wettable powder, suspoemulsion, emulsion in water or water dispersible granules. The herbicide may also contain other conventional components in pesticides, such as stabilizers, chelating agents, dyes, colorants, protective colloids, binders, thickeners, thixotropic agents, penetrants and polymers.

The dosage of the composition of the invention in the herbicide depends on the resistance of the weeds, the method of application and the frequency of application; a person of ordinary skill in the art can determine the appropriate dosage only by conventional experimental methods.

The term "compound of the invention" as used herein refers to the compound of formula (I) in any form, i.e., any salt or non-salt form (e.g., in the form of a free acid or free base, or in the form of a pharmaceutically acceptable salt thereof) and any physical form (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of many forms.

Solvates

For solvates of the compounds of the invention or salts of the compounds in the form of crystals, those skilled in the art will understand that pesticide-acceptable solvates can be formed in which solvent molecules are incorporated into the crystal lattice during crystallization. Solvates may contain non-aqueous solvents such as ethanol, isopropanol, DMSO, acetic acid, ethanolamine, and ethyl acetate, or they may contain water as a solvent (the solvent is incorporated into the crystal lattice). Solvates in which water is the solvent (the solvent is incorporated into the crystal lattice) are often referred to as "hydrates." Hydrates include stoichiometric hydrates and components that contain variable amounts of water. The invention includes such solvates.

The advantages of the invention are as follows:

(1) The polyketone compound 1 and compound 2 with a trans-naphthane ring involved in the invention are new compounds, and it is found for the first time that the polyketone compounds with a trans-naphthane ring have herbicidal activity. At a concentration of 10 μg/mL, the growth inhibition rates of the compound 1 and the compound 2 on the radicles of *Echinochloa crusgalli* seedlings are 81.5% and 79.6%, respectively, which is superior to the commercial herbicide acetochlor and could be used as a lead compound with herbicidal activity or a new pesticide ingredient.

(2) The polyketone compound 1 and compound 2 with a trans-naphthane ring involved in the invention are produced by fermentation of the strain *Penicillium* sp. TR85, which is convenient for large-scale fermentation production; in addition, the compound 1 and the compound 2 are natural products, and have the advantages of good environmental compatibility and low pesticide resistance as compared with chemically synthesized pesticides.

DETAILED DESCRIPTION OF THE INVENTION

Figure 1:
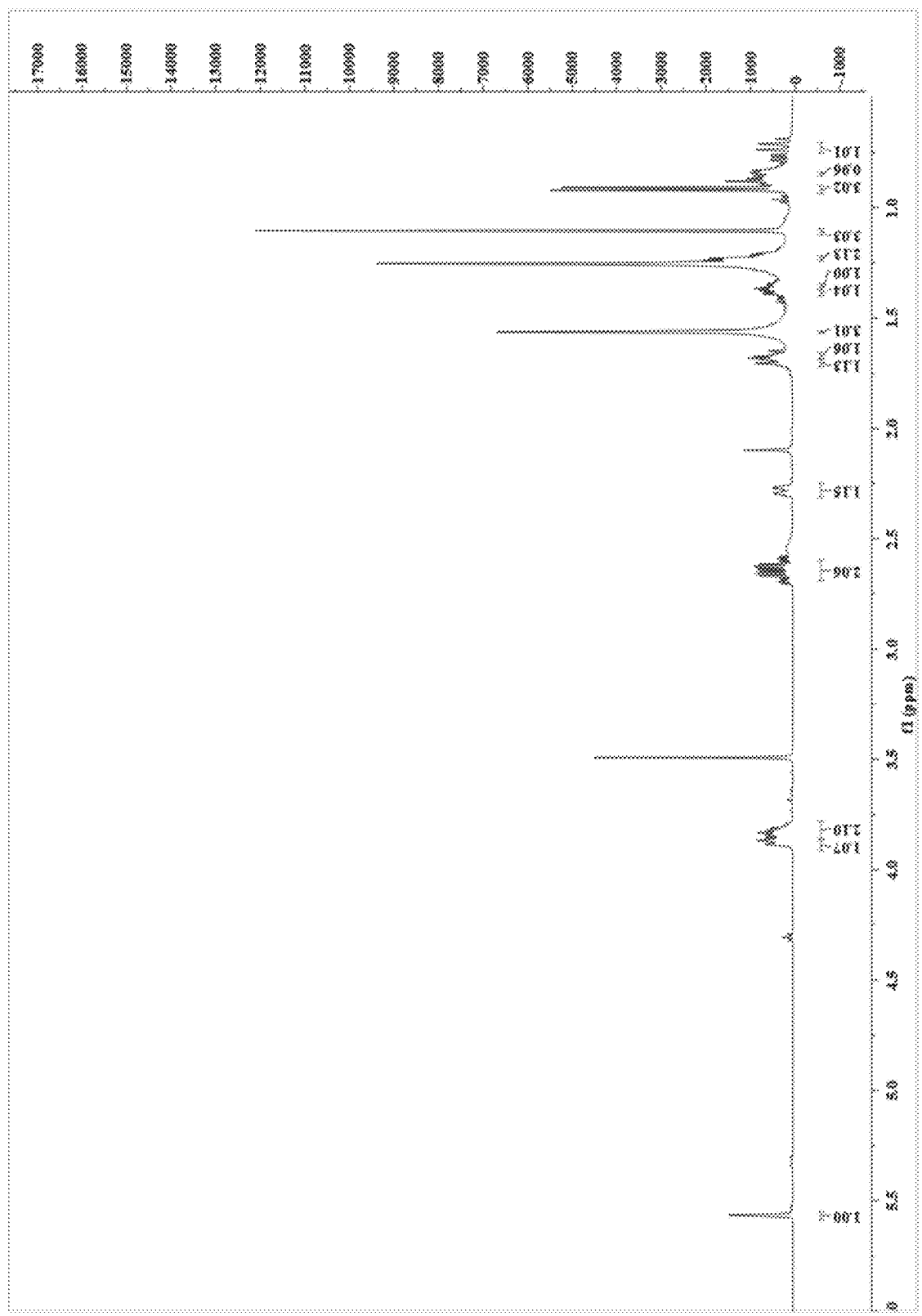
FIG. 1 is a $^1$H NMR spectrum of Compound 1.

Unless otherwise stated, the terms used in the invention generally have the meanings generally understood by those of ordinary skill in the art.

The invention will be described in further detail in conjunction with specific embodiments and with reference to data. The following embodiments are only for illustrating the invention, and are not intended to limit the scope of the invention in any way.

According to the invention, compounds in the following examples are isolated from the fermentation product of the strain *Penicillium* sp. TR85 (deposited on Aug. 2, 2019 at China General Microbiological Culture Collection Center, with CGMCC No. 18116), and the structure of compound 1 and compound 2 is as follows (the Arabic numerals in the structure are the marks of carbon atoms):

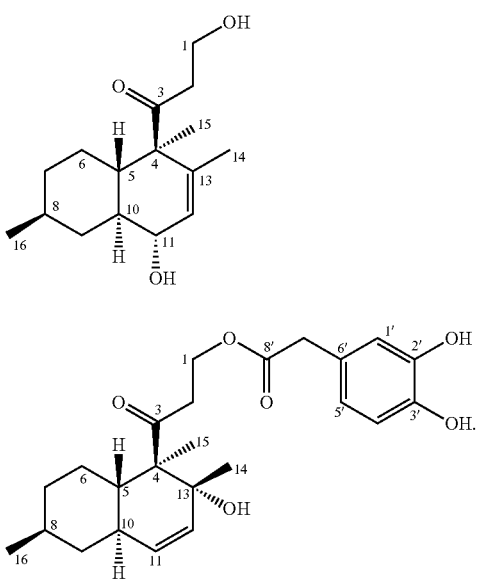

Example 1: Separation and Identification of the Strain *Penicillium* sp. TR85

(1) Strain Separation

The strain TR85 of the invention was isolated from the roots of the saline-alkali tolerant plant *Suaeda glauca*.

Sample collection: *Suaeda glauca* samples were collected from wetlands in the intertidal zone of Jiaozhou Bay in Qingdao;

Separation step: the roots of *Suaeda glauca* samples were washed, soaked in 75% ethanol for 2 min, rinsed with sterile water for 3 to 4 times, and dried up with sterile gauze; the roots of *Suaeda glauca* samples were cut into 0.5 cm pieces and implanted in a PDA double-antibody culture medium plate, 4-5 pieces per dish, and then placed in an incubator, incubated upside down at 28° C., and observed every 24 h; the mycelia at the cut surface were picked, and inoculated in a PDA double-antibody culture medium plate by plate streaking, and after repeated purification, the *Suaeda glauca*-derived strain with the consistent colony morphological characteristics were obtained and numbered for deposition.

The formulation of the PDA dual-antibody culture medium: 20% of potato extract, 2% of glucose and 1.5% of agar were mixed with natural seawater, and added with penicillin potassium with a final concentration of 150 μg/mL and streptomycin sulfate with a final concentration of 120 μg/mL.

(2) Strain Identification

The strain TR85 was inoculated on the surface of the PDA plate and cultured at 28° C. for 5-7 days and observed. The mycelia were white at the beginning, and then produced dark green spores, and were able to produce brownish yellow pigment.

The determination result of the rDNA gene sequence of the strain (ITS-5.8S-ITS2 area) is shown in SEQ ID NO: 1.

The above sequence determination result has a similarity of 99% with the strain *Penicillium viridicatum* (Accession number: MK583349) as compared with the corresponding sequence information of known strains in the Genbank database. The sequence has been submitted to the Genbank database (Accession number: MN100452).

In summary, the strain is identified to be *Pseudomonas* sp., and has been deposited on Aug. 2, 2019 at China General Microbiological Culture Collection Center (CGMCC) (Address: Institute of Microbiology, Chinese Academy of Sciences, No. 3, Yard 1, West Beichen Road, Chaoyang District, Beijing), with CGMCC No. 18116.

Example 2: Preparation Method of Compound 1 and Compound 2

(1) Fermentation Culture of the Strain

The strain *Penicillium* sp. TR85 (2×2 cm in size) grown on the surface of the PDA plate was cut and inoculated into a sterilized Erlenmeyer flask containing a solid medium, and then incubated at room temperature for 30 days. The fermentation product was repeatedly soaked and extracted with ethyl acetate, and extracts were combined and concentrated to obtain a crude fermentation extract.

The solid medium is prepared by adding 100 g of rice and 0.6 g of peptone per 100 mL of natural seawater.

(2) Preparation of the Compound

Reduced-pressure silica gel column chromatography (glass chromatography column having an inner diameter of 65 mm and a length of 300 mm and equipped with a sand plate and a suction nozzle) was carried out on the crude fermentation extract, and gradient elution was carried out with a solvent (petroleum ether-ethyl acetate at a gradient of 40:1 to 1:1 ((v/v), the same below) in order of increasing polarity of the eluent; an eluting fraction in the case of the petroleum ether-ethyl acetate at a gradient of 1:1 was collected and subjected to reversed-phase silica gel column chromatography (glass chromatography column having an inner diameter of 30 mm and a length of 600 mm and equipped with a standard PTFE door) and gradient elution with a solvent (a methanol-water solution at a gradient of 2:8 to 1:0) was carried out.

A reversed-phase silica gel eluting fractions in the case of methanol-water at a gradient of 6:4 was collected and purified by semi-preparative high performance liquid chromatography with 50% methanol-water as a mobile phase, the detection wavelength of 220 nm, and the flow rate of 3 mL/min, and the fraction with retention time $t_R$ of 14.4 min was collected, thus obtaining compound 1.

A reversed-phase silica gel eluting fractions in the case of methanol-water at a gradient of 8:2 was collected and purified by semi-preparative high performance liquid chromatography with 76% methanol-water as a mobile phase, the detection wavelength of 220 nm, and the flow rate of 3 mL/min, and the fraction with retention time $t_R$ of 12.5 min was collected, thus obtaining compound 2.

(3) Structural Identification of the Compound

TABLE 1

$^1$H (500 MHz) and $^{13}$C NMR (125 MHz) of Compound 1 Spectral data (solvent used for NMR test: deuterated chloroform)

| position | $\delta_C$ (type) | $\delta_H$ (mult., J in Hz) |
| --- | --- | --- |
| 1 | 58.7, CH$_2$ | 3.83, m |
| 2 | 39.6, CH$_2$ | 2.64, m |
| 3 | 215.4, C | |
| 4 | 57.6, C | |
| 5 | 41.6, CH | 1.67, m |
| 6 | 27.2, CH$_2$ | 1.22, m |
| 7 | 34.6, CH$_2$ | 0.84, m; 1.70, m |

TABLE 1-continued $^1$H (500 MHz) and $^{13}$C NMR (125 MHz) of Compound 1 Spectral data (solvent used for NMR test: deuterated chloroform)

| position | $\delta_C$ (type) | $\delta_H$ (mult., J in Hz) |
|---|---|---|
| 8 | 31.8, CH | 1.36, m |
| 9 | 40.1, CH$_2$ | 0.72, m; 2.28, m |
| 10 | 40.7, CH | 1.39, m |
| 11 | 73.8, CH | 3.88, m |
| 12 | 128.7, CH | 5.56, d (1.4) |
| 13 | 137.9, C | |
| 14 | 19.7, CH$_3$ | 1.56, s |
| 15 | 15.6, CH$_3$ | 1.11, s |
| 16 | 22.6, CH$_3$ | 0.90, d (6.5) |

TABLE 2

$^1$H (500 MHz) and $^{13}$C NMR (125 MHz) of Compound 2 Spectral data (solvent used for NMR test: deuterated methanol)

| position | $\delta_C$ (type) | $\delta_H$ (mult., J in Hz) |
|---|---|---|
| 1 | 61.0, CH$_2$ | 4.27, m |
| 2 | 41.8, CH$_2$ | 2.83, dt (4.3, 9.6); 3.11, m |
| 3 | 213.9, C | |
| 4 | 58.4, C | |
| 5 | 44.8, CH | 1.73, m |
| 6 | 28.4, CH$_2$ | 1.48, m |
| 7 | 36.7, CH$_2$ | 0.99, m; 1.73, m |
| 8 | 34.6, CH | 1.44, m |
| 9 | 43.0, CH$_2$ | 0.76, m; 1.79, m |
| 10 | 39.8, CH | 1.79, m |
| 11 | 131.1, CH | 5.33, m |
| 12 | 134.9, CH | 5.33, m |
| 13 | 74.2, C | |
| 14 | 27.9, CH$_3$ | 1.02, s |
| 15 | 12.4, CH$_3$ | 1.27, s |
| 16 | 22.8, CH$_3$ | 0.90, d (4.8) |
| 1' | 117.4, CH | 6.69, s |
| 2' | 146.3, C | |
| 3' | 145.5, C | |
| 4' | 116.3, CH | 6.67, m |
| 5' | 121.6, CH | 6.54, dd (8.1, 2.1) |
| 6' | 126.9, C | |
| 7' | 41.4, CH2 | 3.41, s |
| 8' | 174.0, C | |

Figure 2:
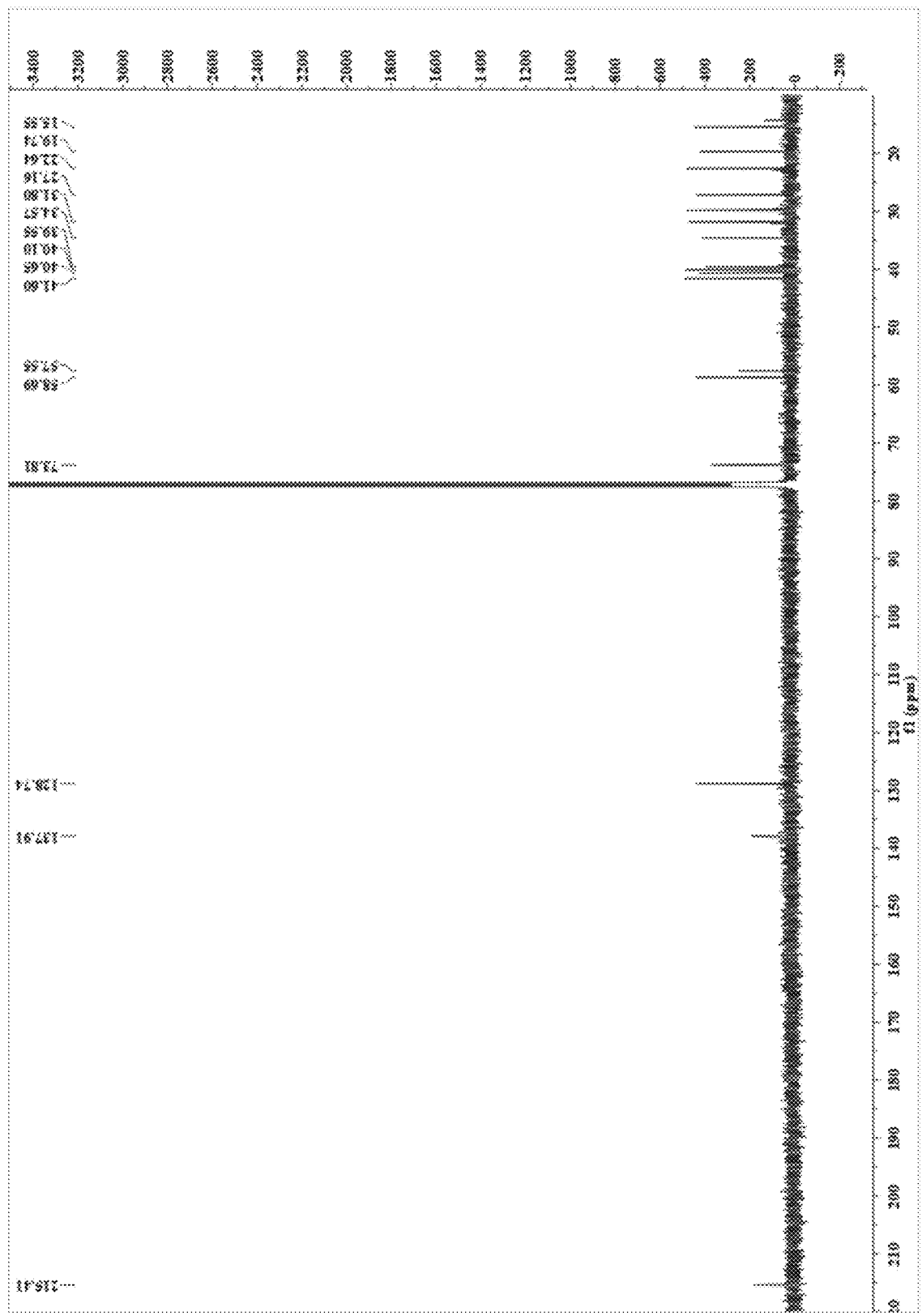
FIG. 2 is a $^{13}$C NMR spectrum of Compound 1.

Compound 1, white powder, HR-ESI-MS m/z 289.1741 [M+Na]$^+$, suggesting that the molecular formula is $C_{16}H_{26}O_3$, and its $^1$H- (FIG. 1) and $^{13}$C-NMR (FIG. 2) data are shown in Table 1.

Figure 3:
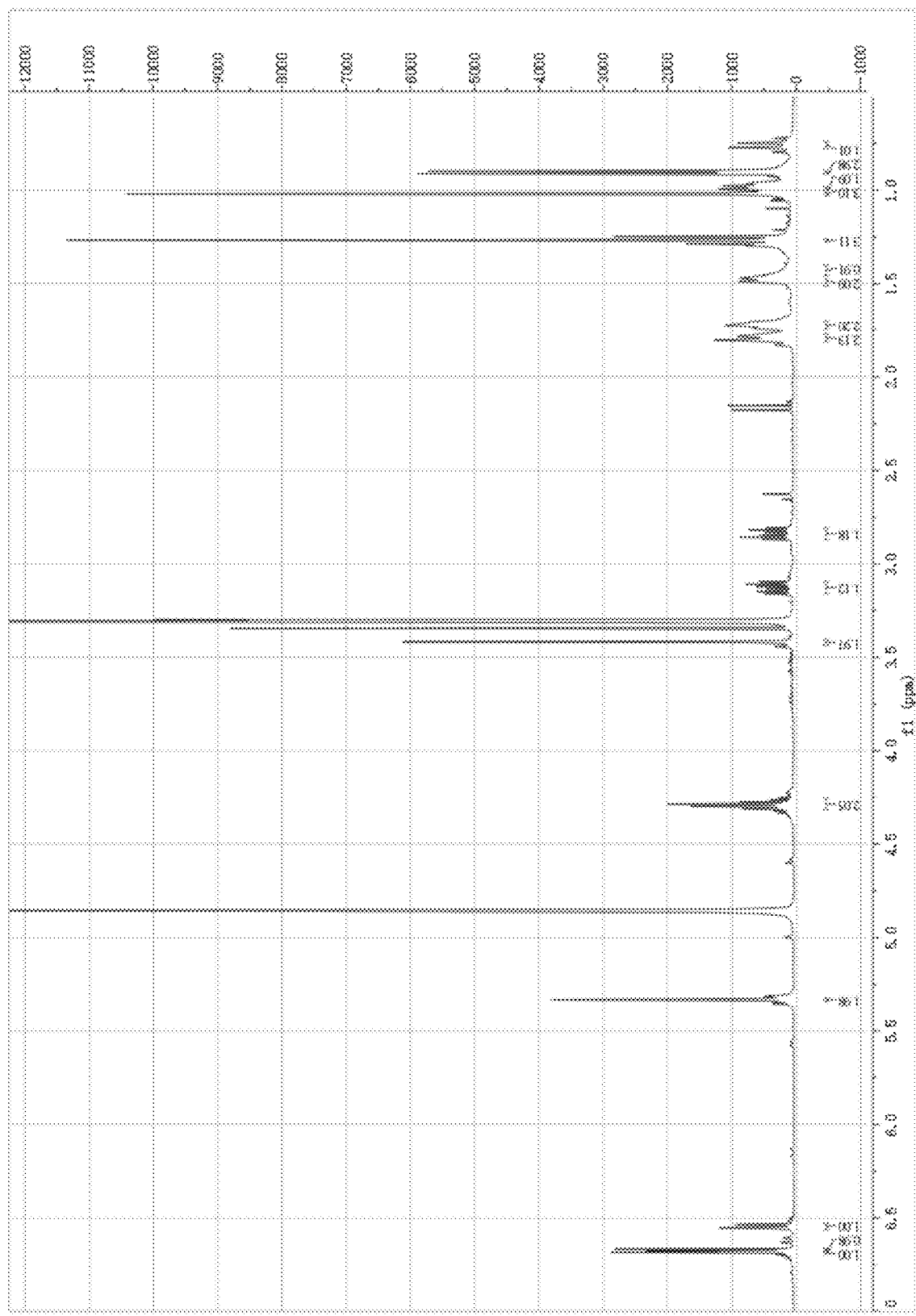
FIG. 3 is a $^1$H NMR spectrum of Compound 2.
Figure 4:
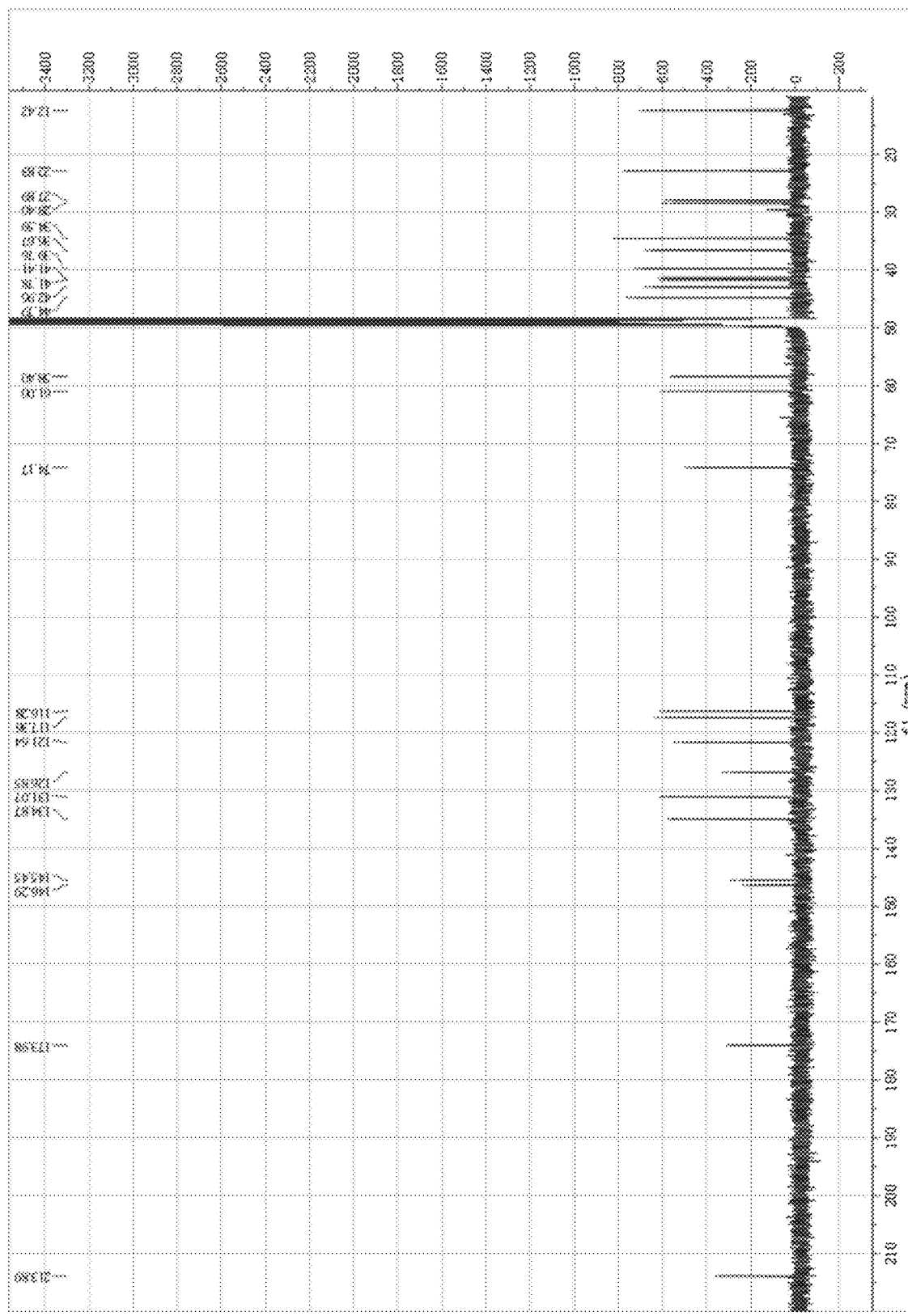
FIG. 4 is a $^{13}$C NMR spectrum of Compound 2.

Compound 2, light yellow powder, HR-ESI-MS m/z 439.2107 [M+Na]$^{30}$, suggesting that the molecular formula is $C_{24}H_{32}O_6$, and its $^1$H- (FIG. 3) and $^{13}$C-NMR (FIG. 4) data are shown in Table 2.

Example 3: Herbicidal Activity Test

The method of grinded plant tissue powder mixed with agar (PPA method), established by Luo Xiaoyong, et al. (Journal of Qingdao Agricultural University, 2007, 24: 267-270) is used to quickly determine the herbicidal activity of compounds. It has the advantages of high sensitivity, easy operation, good repeatability, and large-throughput screening. It is also easy to observe the growth status of indicator plants. Luo Xiaoyong used this method to quickly determine the herbicidal activity of the leaves of 40 garden plants. Zhang Lijuan (Plant Protection, 2016, 42: 63-66) and Su Fansheng (Applied Chemistry, 2014, 31: 290-295) quickly determined the herbicidal activity of corn stalks and imidazole compounds by the PPA method with Echinochloa crusgalli as the test weed. Zhang Yun (Journal of Microbiology, 2015, 55: 292-298) and Li Shuai (Journal of Agricultural and Food Chemistry, 2014, 62: 8997-9001) studied the inhibitory effect of microbial secondary metabolites on the root growth of Amaranthus retroflexus by using Amaranthus retroflexus as the test weed.

(1) Germination of Weed Seeds

Weed seeds were first sterilized with 0.2% sodium hypochlorite for 15 min, then washed repeatedly with sterile distilled water, soaked for 4-6 h, and germinated for 12 h in a medical tray with sterile wet filter paper in a dark place.

(2) Preparation of Sample Solution

The compound to be tested was dissolved in dimethyl sulfoxide (DMSO) to obtain a 4 mg/mL solution, and the 4 mg/mL solution was then diluted with 50% DMSO aqueous solution to different concentrations for later use.

(3) Test Method 1 mL of the sample solution and 99 mL of sterile agar aqueous solution were mixed well, and poured into three 25 mL small beakers to be condensed. Needle-nose tweezers were used to insert 5 small holes on the surface of the condensed agar, the germinated test weed seedlings with 4-5 radicles were clamped separately and inserted gently and vertically into the small holes. Each beaker had five pieces of such agar and the operation was repeated for three times. Then, all beakers were sealed with tin foil and placed in a sterilized small carton, and the sterilized small carton was then placed in an artificial climate box for shading culture for 2 days. The artificial climate box set an automatic cycle of 14 h lighting (25° C.) and 10 h shading (20° C.), and the relative humidity in the box was set at 60%. After 2 days, the lengths of the radicle and hypocotyl were investigated to calculate the weed growth inhibition rate.

The calculation equations were as follows (Chinese Agricultural Science Bulletin, 2013, 29: 177-182):

Growth=length of radicle (hypocotyl) after treatment–length of radicle (hypocotyl) before treatment;

Inhibition rate (%)=[(average growth of control–average growth of treatment)/average growth of control]×100%.

TABLE 3

Growth inhibition rates (%) of compound 1 and compound 2 to radicles of Echinochloa crusgalli seedlings

| | 10 µg/mL | 5 µg/mL | 2.5 µg/mL |
|---|---|---|---|
| Compound 1 | 81.5 ± 2.0a | 64.7 ± 0.9a | 52.7 ± 1.0b |
| Compound 2 | 79.6 ± 1.1b | 55.4 ± 1.2b | 41.0 ± 0.8c |
| Acetochlor | 76.1 ± 1.4c | 65.6 ± 1.8a | 54.8 ± 1.3a |

Note:
There are significant differences P < 0.05 between different letters in the same line.

Figure 5:
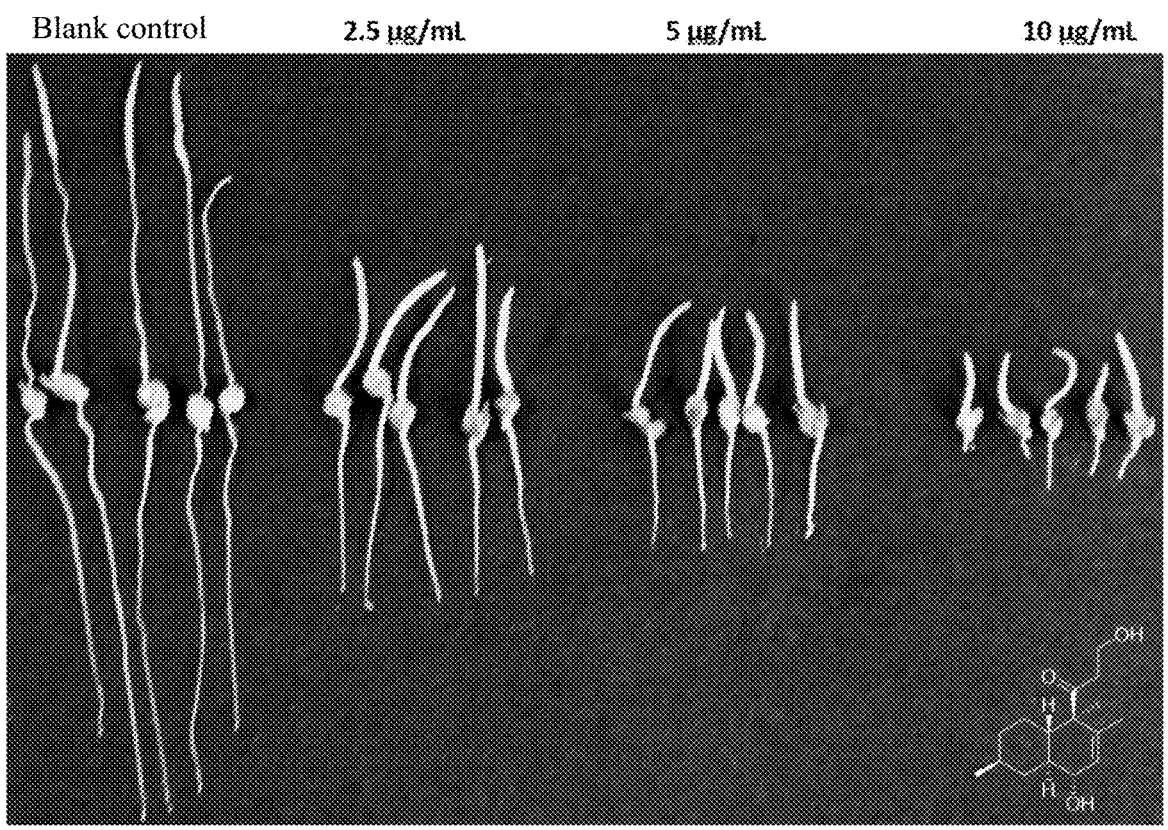
FIG. 5 shows the inhibitory effect of Compound 1 on the growth of *Echinochloa crusgalli* seedlings.
Figure 6:
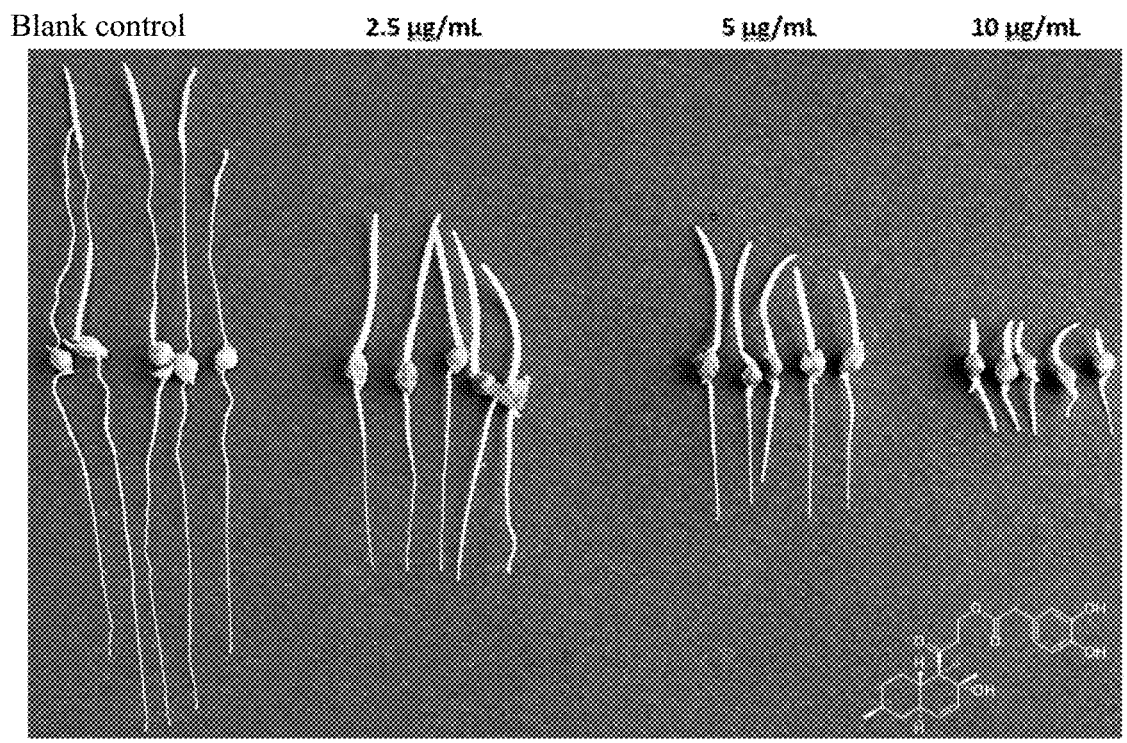
FIG. 6 shows the inhibitory effect of Compound 2 on the growth of *Echinochloa crusgalli* seedlings.

The test results are shown in Table 3. The results show that at a concentration of 10 µg/mL, the growth inhibition rates (%) of compound 1 (FIG. 5) and compound 2 (FIG. 6) to radicles of E. crusgalli seedlings are 81.5% and 79.6%, significantly better than that of the commercial herbicide acetochlor, so compound 1 and compound 2 can be used as lead compounds with herbicidal activity or new pesticide ingredients.

Example 4: Lethal Activity of Brine Shrimp

Brine shrimp is an aquatic animal that is highly sensitive to toxic substances. It can be used as a model organism to preliminary evaluate the toxic effects of compounds on the environment. Masi, M. et al. used Brine shrimp to preliminary evaluate the toxicity of the herbicidal active compounds Colletochlorins E and F (Journal of Agricultural and Food Chemistry, 2017, 65: 1124-1130).

1) Hatching of Brine Shrimp Eggs 100 mg of Brine shrimp eggs were placed in a 500 mL beaker, 400 mL of artificial seawater was added, the Brine shrimp eggs were slowly inflated with an air pump and hatched at room temperature for 24 h, the egg shells and unhatched eggs were removed, and the Brine shrimps were further incubated for 24 h.

2) Preparation of Sample Solution

The compound to be tested was dissolved in DMSO to obtain a 20 mg/mL mother liquor, and the mother liquor was then sequentially diluted twice to obtain 10, 5 and 2.5 mg/mL solutions for later use.

3) Test Method

195 μL of artificial seawater containing 10-15 Brine shrimps were added into each well of a 96-well cell culture plate to make a test culture plate. The blank control group and the sample group of each concentration are each placed in three parallel wells, the blank control group was added with 5 μL of artificial seawater, and the sample groups were added with 5 μL of sample solutions of different concentrations. After incubation at room temperature for 24 h, the number of Brine shrimp deaths was counted under a binocular dissecting microscope.

The lethal activity of Brine shrimp was expressed by corrected mortality, and its calculation equation is as follows:

Corrected mortality=(survival rate of control group-survival rate of treatment group)/survival rate of control group×100%, and the $LD_{50}$ value was also calculated.

The test results show that the compounds 1 and 2 do not exhibit the lethal activity of Brine shrimp even at the concentration of 500 μg/mL. The above results can preliminarily show that the compounds 1 and 2 have less toxic effect on the environment and has the potential for agricultural extension.

The specific embodiments described above further explain the objectives, technical solutions and beneficial effects of the invention. It should be understood that the above description is only the specific embodiments of the invention, and is not intended to limit the scope of the invention. Any modifications, equivalents, improvements and the like made without departing from the spirit and principle of the invention should be included in the scope of the invention.

What is claimed is:

1. A method of isolating a compound 1 and a compound 2, comprising:

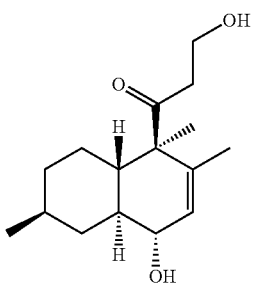

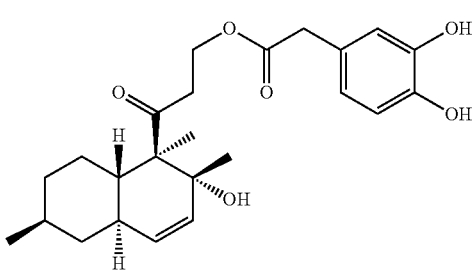

providing *Penicillium* sp. TR85;
inoculating the *Penicillium* sp. TR85 into a sterilized solid medium;
resting for fermentation at room temperature, and
obtaining a fermentation product,
wherein the fermentation product includes the compound 1 and the compound 2.

2. The method of claim 1, wherein the sterilized solid medium includes rice, peptone and see water in a ratio of 100 g:0.6 g:100 mL.

3. The method of claim 1, further comprising:
(1) soaking and extracting the fermentation product with ethyl acetate to obtain extracts, and combining and concentrating the extracts to obtain a crude fermentation extract;
(2) carrying out a reduced-pressure silica gel column chromatography on the crude fermentation extract, performing a gradient elution with an eluent: petroleum ether:ethyl acetate at a gradient of 40:1 to 1:1 (v/v), collecting an eluting fraction when the petroleum ether:ethyl acetate is at a gradient of 1:1, carrying out a reversed-phase silica gel column chromatography, and performing a gradient elution with a second eluent: methanol:water solution at a gradient of 2:8 to 1:0 (v/v));
(3) collecting reversed-phase silica gel eluting fractions when methanol:water is at a gradient of 6:4 (v/v), carrying out a semi-preparative high performance liquid chromatography with 50% methanol in water as a mobile phase, a detection wavelength of 220 nm, and a flow rate of 3 mL/min, and collecting fractions with a retention time $t_R$ of 14.4 min, thus obtaining the compound 1; and
(4) collecting reversed-phase silica gel eluting fractions when the methanol:water is at a gradient of 8:2 (v/v), carrying out a semi-preparative high performance liquid chromatography with 76% methanol in water as a mobile phase, a detection wavelength of 220 nm, and a flow rate of 3 mL/min, and collecting fractions with retention time $t_R$ of 12.5 min, thus obtaining the compound 2.

4. An herbicidal composition comprising:
a compound 1 or a compound 2

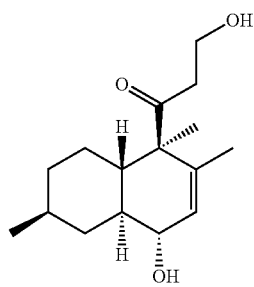

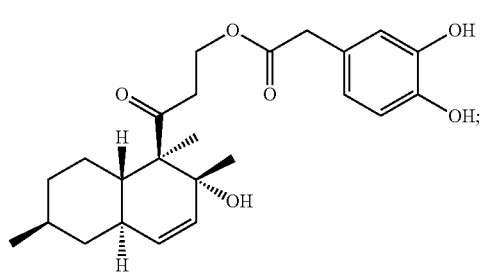

and
pesticide-acceptable adjuvants.

5. The herbicidal composition of claim 1, wherein the pesticide-acceptable adjuvants are selected from the group consisting of carriers, surfactants and safeners.

6. The herbicidal composition of claim 1, wherein the herbicidal composition further comprises one or more selected from the group consisting of a stabilizer, a chelating agent, a dye, a colorant, a protective colloid, a binder, a thickener, a thixotropic agent, a penetrant and a polymer.

7. The herbicidal composition of claim 1, wherein the herbicidal composition is an oil, an emulsion, a suspension, or a wettable powder.

* * * * *

SEQUENCE LISTING

<160> NUMBER OF SEQ ID NOS: 1

<210> SEQ ID NO 1
<211> LENGTH: 561
<212> TYPE: DNA
<213> ORGANISM: Penicillium sp.

<400> SEQUENCE: 1

```
tccgtaggtg aaccttgcgg ttggggtcca acctcccacc cgtgtttatt ttaccttgtt      60
gcttcggcgg gcccgccttt actggccgcc gggggctca cgccccggg cccgcgcccg      120 ccgaagacac cctcgaactc tgtctgaaga ttgaagtctg agtgaaaata taaattattt     180
aaaactttca acaacggatc tcttggttcc ggcatcgatg aagaacgcag cgaaatgcga     240
tacgtaatgt gaattgcaaa ttcagtgaat catcgagtct tgaacgcac attgcgcccc     300 ctggtattcc gggggcatg cctgtccgag cgtcattgct gccctcaagc ccggcttgtg     360
tgttgggccc cgtcctccga ttccggggga cgggcccgaa aggcagcggc ggcaccgcgt     420
ccggtcctcg agcgtatggg gctttgtcac ccgctctgta ggcccggccg gcgcttgccg     480
atcaacccaa atttttatcc aggttgacct cggatcaggt agggataccc gctgaactta     540
agcatatcaa taagcggagg a                                              561
```